United States Patent [19]
Virag

[11] 3,993,066
[45] Nov. 23, 1976

[54] BURETTE CHAMBER FOR USE WITH INTRAVENOUS SOLUTION ADMINISTRATION SET

[75] Inventor: Robert A. Virag, Lake Zurich, Ill.

[73] Assignee: Baxter Laboratories, Inc., Morton Grove, Ill.

[22] Filed: Nov. 1, 1974

[21] Appl. No.: 520,062

[52] U.S. Cl. .................. 128/214 C; 128/214.2; 137/576; 222/159
[51] Int. Cl.² .......................................... A61M 5/14
[58] Field of Search ......... 128/214 R, 214 C, 214.2, 128/227, 272; 73/198; 222/56, 159, 456; 137/574, 576; 215/100 R, 6

[56] References Cited
UNITED STATES PATENTS

| 1,205,410 | 11/1916 | Tenney | 128/214 R |
|---|---|---|---|
| 3,204,633 | 9/1965 | Hofstra | 128/214 E |
| 3,216,419 | 11/1965 | Scislowicz | 128/214 C |
| 3,527,251 | 9/1970 | Hagstrom et al. | 137/576 |
| 3,776,229 | 12/1973 | McPhee | 128/214 C |
| 3,778,973 | 12/1973 | Martinez | 55/199 |
| 3,869,771 | 3/1975 | Bollinger | 128/188 |
| 3,929,157 | 12/1975 | Serur | 128/214 C X |
| 3,931,818 | 1/1976 | Goldowsky | 128/214 C |

FOREIGN PATENTS OR APPLICATIONS

| 1,182,016 | 2/1970 | United Kingdom | 128/214 C |

*Primary Examiner*—Dalton L. Truluck
*Attorney, Agent, or Firm*—Louis Altman; George H. Gerstman

[57] ABSTRACT

A burette chamber is provided which includes a primary and a secondary compartment, a wall member separating the primary and secondary compartments with the wall member providing an opening for communication between the primary and secondary compartments. When the burette chamber is included in an intravenous solution administration set, the set can continuously administer IV solution to a patient as well as to allow intermittent administration of medicaments with return to the continuous administration of IV solution to the patient after completion of medicament administration.

7 Claims, 8 Drawing Figures

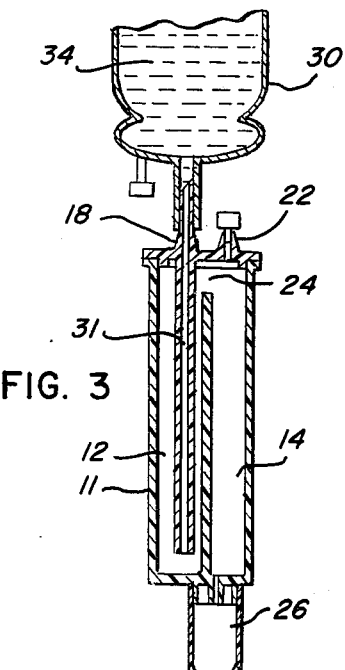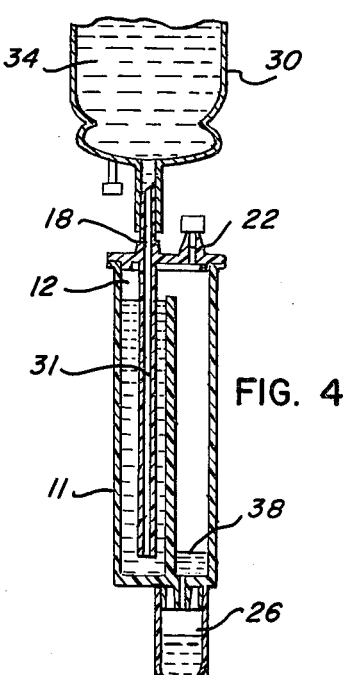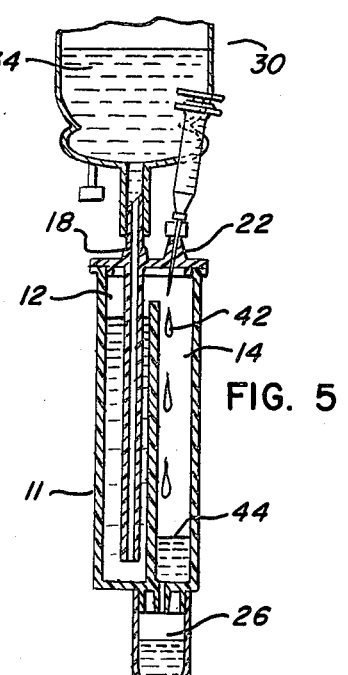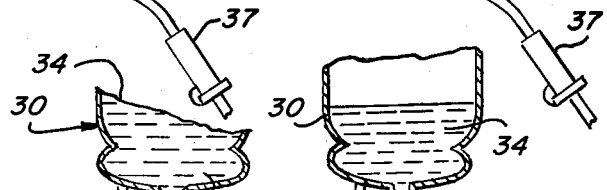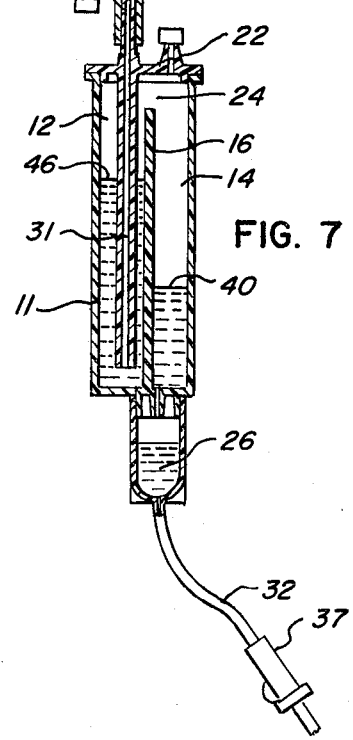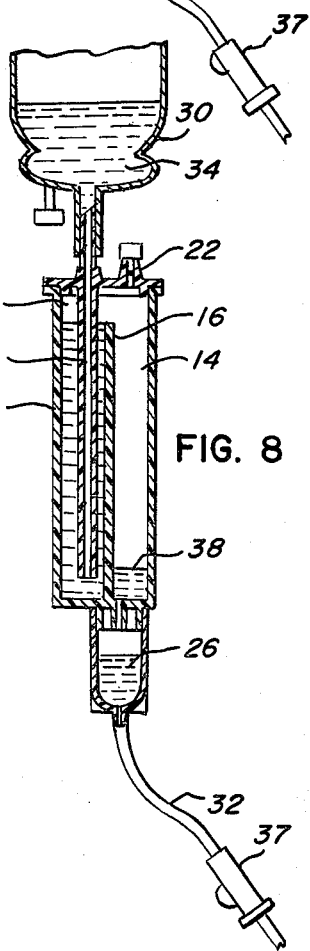

BURETTE CHAMBER FOR USE WITH INTRAVENOUS SOLUTION ADMINISTRATION SET

BACKGROUND OF THE INVENTION

This invention relates to an improved burette chamber for use with an administration set in giving intravenous (IV) solutions to a patient. The term "administration set" and "set" as used herein mean all of the apparatus necessary to transport an IV solution from an IV solution source (such as a bottle or plastic container) to the patient. Generally this apparatus includes at one end a spike or other piercing device for entering an intravenous solution source and at the opposite end a needle which can be inserted in the vein of a patient. Between the spike and needle an administraion set usually includes a flow rate regulator (e.g., a roller clamp such as the one described in U.S. Pat. No. 3,099,429) and a drip chamber. The drip chamber provides a way for hospital personnel to observe or count the numbers of drops of IV solution being administered to the patient. Other items may be added to the administration set, such as injection sites, flashback indicators, Y-sites and the like.

This invention is particularly concerned with situations where it is necessary or desirable to intermittently administer some medicament to the patient during the course of the administration of an IV solution. Presently a technique for doing this employs a burette chamber in the administration set. A Buretrol burette solution administration set available from Travenol Laboratories, Inc., Morton Grove, Illinois is an example. A Buretrol burette chamber is inserted in the administration set upstream of the drip chamber. The burette chamber has two operative positions. In one position, the chamber will dispense preselected volumes of IV solution mixed with a medicament. Once all the medicament is dispensed, flow ceases until someone performs a series of steps necessary to convert the chamber to its other operative position. In the other operative position, IV solution simply flows through the burette chamber and into the drip chamber. In this position, the IV solution is not acted upon by the burette chamber, but the chamber is in position for and can be used to administer drugs or the like.

Using the burette chambers now commerically available, it is necessary for hospital personnel to personally be present to adjust the burette for drug or medicament administration and then personally be present after medicament administration to readjust the burette chamber to its other operative position and thereby restart the flow of the IV solution being administered.

The burette chamber of this invention eliminates the need for the personal attention of hospital personnel to reinitiate IV flow after medicament administration. It also provides a closed, airtight chamber for the mixing of medicaments. It requires no venting to the atmosphere outside of the burette chamber.

It is, therefore, an object of the present invention to provide an administration set capable of the continuous administration of IV solution to a patient with a minimum number of steps.

Another object of the present invention is to provide for the injection of medicament as required during the continuous administration of IV solution to a patient.

A further object of the present invention is to provide for the automatic return to the continuous administration of IV solution to a patient after the administration of medicament.

Other objects and advantages of the invention will become apparent as the description proceeds.

BRIEF DESCRIPTION OF THE INVENTION

In accordance with the present invention, there is provided a burette chamber which includes a airtight container having a wall member separating the container into a primary compartment and a secondary compartment. The burette chamber is also provided with a first inlet connected to the container and communicating with the primary compartment. Means are provided for coupling the first inlet to a primary solution container or IV solution source. The burette chamber also includes an injection site which communicates with the secondary compartment of the burette chamber. The wall member defines an opening for communication between the primary and secondary compartments. The chamber is also provided with a drip chamber that serves as an outlet from the chamber.

In the illustrative embodiment of the invention, the burette chamber includes a tube connected to the first inlet and extending downwardly therefrom to a lower portion of the primary compartment. An injection site communicates with the secondary compartment. Molded volume indicia are provided on the burette chamber and the primary and secondary compartments may be provided with different light-transmissive surfaces.

In the operation of the present invention, the burette chamber is included in an administration set. The chamber outlet is connected to the set tubing leading to the patient. A primary solution container containing primary IV solution is connected by tubing to the first inlet of the chamber. The primary solution is permitted to flow into the primary compartment and fill it with primary solution. The primary solution is further permitted to spill over into the secondary compartment of the container until pressure equilibrium is reached.

In the illustrative embodiment, when desired, medicament is injected into the burette chamber injection site where it can mix with the primary solution in the secondary compartment of the container. This addition of more fluid (medicament) to the closed burette chamber causes a pressure imbalance in the chamber. Pressure equilibrium is, however, automatically restored by an amount of the primary solution in the primary container (an amount equal to the amount of medicament added) being displaced up the tube leading into the primary compartment and back into the primary solution container. The medicament can then be diluted (if desired) with a volume of primary fluid by tilting the burette chamber and spilling primary solution from the primary compartment to the secondary compartment.

Thereupon, the mixture of the medicament and primary solution in the secondary compartment is permitted to flow from the outlet to the patient. This provides a method of automatic, continuous administration of the primary solution to a patient because the primary solution level will rise in the primary compartment and spill over into the secondary compartment when the mixture of the medicament and the primary solution in the secondary compartment has been administered from the outlet to the patient.

A more detailed explanation of the invention is provided in the following description and claims, and is illustrated in the accompanying drawings.

BRIEF DESCRIPTION OF THE DRAWINGS

FIG. 3 is a front, cross-sectional view of the administration set with a primary solution container connected to the set and a conventional IV clamp attached to an outlet tube;

FIG. 4 is a similar view thereof, indicating that pressure equilibrium has been attained;

FIG. 5 is a similar view thereof, depicting the injection of medicament into the injection site;

FIG. 6 is a similar view thereof, showing how the medicament can be diluted with primary solution by tilting the set until the primary solution spills over into the secondary compartment and is mixed with the medicament;

FIG. 7 is a similar view thereof, showing intermittent administration of the medicament injected in FIG. 5; and FIG. 8 is a similar view thereof, showing the automatic return to the continuous administration of primary solution after the mixture of medicament and primary solution is dispensed to the patient.

DETAILED DESCRIPTION OF THE ILLUSTRATIVE EMBODIMENT

Figure 1:
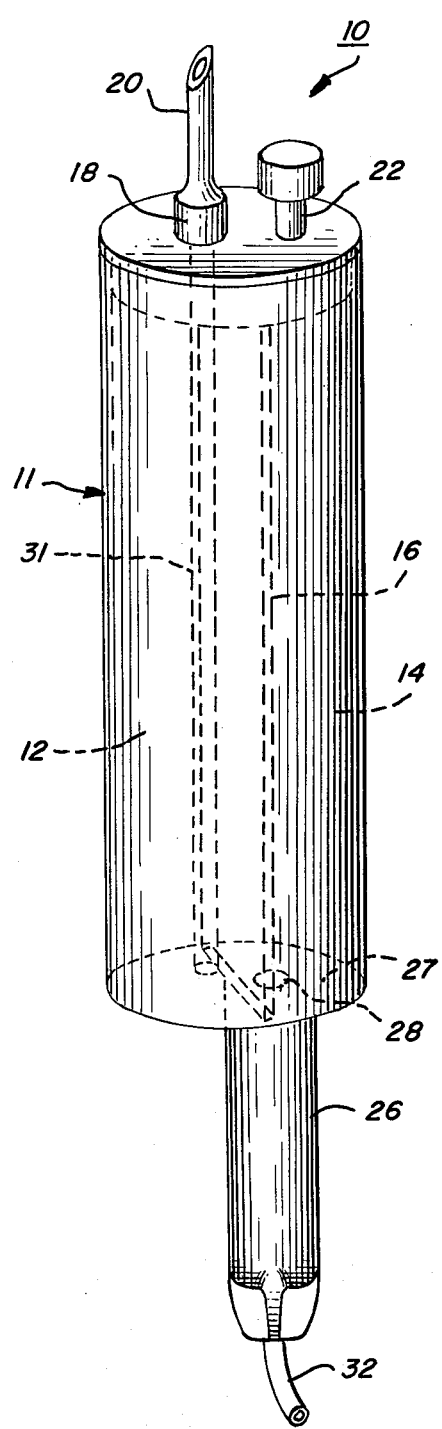
FIG. 1 is a perspective view of an administration set constructed in accordance with the principles of the present invention.
Figure 2:
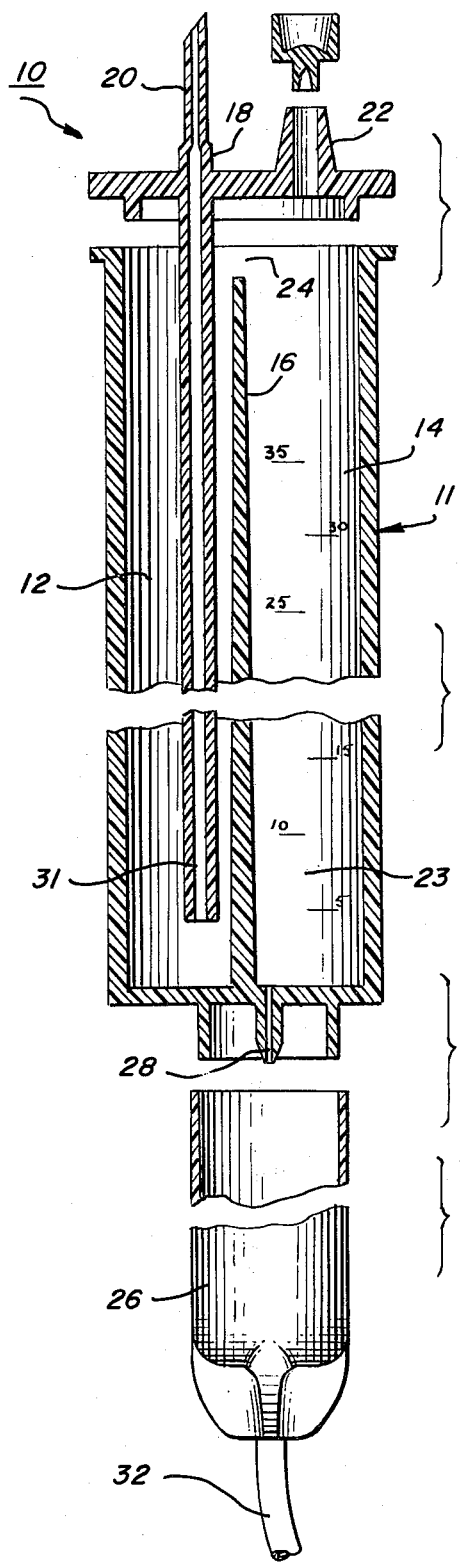
FIG. 2 is an exploded, cross-sectional view thereof.

Referring to the drawings, the burette chamber 10 includes a closed, airtight container 11, with a wall member 16 separating the airtight container 11 into a primary compartment 12 and a secondary compartment 14. A first inlet 18 is connected to the container 11 and communicates with the primary compartment 12. A standard connector 20 is provided for coupling the first inlet 18 to a primary solution container 30 (see FIGS. 3–8).

An injection site 22 is connected to container 11 and communicates with secondary compartment 14. Wall member 16 provides an opening 24 for communication between primary compartment 12 and secondary compartment 14. A drip chamber 26 is connected to the airtight container 11 forming an outlet 28 therewith. A tube 31 is connected to first inlet 18 and extends downwardly therefrom to the lower portion of the primary compartment 12.

Burette chamber 10 is preferably constructed with volume indicia 23 molded onto the outside surface of the secondary compartment 14. The molded volume indicia 23 gives absolute, distortion-free dimensional and volumetric stability during the priming and administration operations.

It is preferred that the primary compartment 12 and the secondary compartment 14 have different light-transmissive surfaces to aid in seeing clearly the different solution levels in the respective compartments. For example, the surface of primary compartment 12 could be translucent while the surface of secondary compartment 14 could be transparent.

As seen in FIG. 1, a hydrophilic membrane valve 27 is provided at the outlet 28 of the apparatus, the purpose of which is to filter particles from the medicament and prevent the infusion of air into the apparatus when the secondary compartment runs dry, for example, when IV solution container 30 is empty or is changed.

Referring to FIG. 3, a primary solution container 30 containing primary IV solution 34 is connected to connector 20. The primary solution 34 flows down tube 31, filling primary compartment 12. The primary solution 34 will then spill over wall member 16 at the opening 24 into secondary compartment 14 until pressure equilibrium is reached with the pressure equilibrium level being depicted in FIG. 4.

In FIG. 5, the injection of medicament 42, as necessary, is administered by the insertion of a syringe 40 into injection site 22. The medicament 42 mixes with the primary solution 34 in the secondary compartment 14. To maintain pressure equilibrium, the primary solution 34 in primary compartment 12 is automatically displaced by reducing the level of the primary solution 34 in the primary compartment 12, with the primary solution 34 being displaced up tube 31 into the primary solution container 30.

In FIG. 6, the mixture of the primary solution 34 and the medicament 42 in the secondary compartment 14 can be diluted further, if desired, by tilting the administration apparatus 10 until the primary solution 34 in the primary compartment 12 spills over into the secondary compartment 14.

Referring to FIGS. 7 and 8, as the level of the mixture of the medicament 42 and the primary solution 34 in the secondary compartment lowers as it is dispensed to the patient, the primary solution level 46 in the primary compartment 12 rises, spilling over wall member 24 into the secondary compartment 14 as the mixture of the medicament 42 and the primary solution 34 in the secondary compartment 14 is being dispensed to the patient. FIG. 8 shows the automatic return to the continuous administration of the primary solution 34 to the patient after the mixture of the medicament 42 and the primary solution 34 in the secondary compartment 14 has been dispensed to the patient.

The step-by-step operation of the apparatus is as follows. Referring to FIG. 3, a conventional IV administration set clamp 37 is placed in an open position on outlet tube 32. A primary solution container 30 containing primary solution is connected to connector 20. The primary solution 34 flows down the tube 31 into the primary compartment 12. The primary solution 34 rises up and fills the primary compartment 12 and spills over the wall member 16 at the opening 24 into the secondary compartment 14 until the level in the secondary compartment 14 reaches a point where pressure equilibrium is attained in the closed chamber 10. The pressure equilibrium level is illustrated in FIG. 4.

The primary solution flows out of the secondary compartment 14 through the outlet 28, the drip chamber 26 and tube 32. The clamp 37 is now closed and the apparatus is properly primed for the administration of the primary solution to a patient via a needle (not shown) attached to the set downstream of the clamp 37.

Referring to FIG. 4, the outlet tube 32 is connected to a patient by inserting the needle in a vein while clamp 37 is closed. The primary solution may now be administered to a patient by opening clamp 37, allowing for continuous administration of the primary solution at the flow rate desired. Typically, clamp 37 is opened only partially, to permit a gradual flow while the hospital personnel adjust the flow to the desired rate by observing the number of drops of IV solution per minute falling into the drip chamber 26.

As the primary solution in the primary compartment 12 continues to spill over the wall member 16 through the opening 24 into the secondary compartment 14, a constant solution level 38 is maintained. The burette chamber will therefore permit continuous administration of primary solution to the patient.

Referring to FIG. 5, the administration of medicament, as necessary, is accomplished as follows. Hospital personnel close clamp 37. The needle of syringe 40 is inserted into injection site 22 and medicament 42 is injected into the primary solution in the secondary compartment 14. This causes the level of the mixture of medicament and primary solution to rise to the level 44. To maintain pressure equilibrium as the medicament 42 is being added, the primary solution in primary compartment 12 is automatically displaced up tube 31 into the primary solution container 30.

Referring to FIG. 6, hospital personnel can further dilute the medicament — IV solution mixture in the secondary compartment 14 by tilting the burette chamber as indicated so that a desired amount of primary solution in the primary compartment 12 spills over into the secondary compartment 14 until the proper mixture of medicament 42 and primary solution in the secondary compartment 14 is attained. Indicia 23, of course, would be used to determine when the desired amount of dilution is attained.

Referring to FIGS. 7 and 8, hospital personnel now open the clamp 37 so that the mixture of the medicament 42 and the primary solution in the secondary compartment 14 will be automatically dispensed to the patient. As this mixture is being administered, the mixture level 40 in the secondary compartment 14 will fall and the primary solution level 46 in the primary compartment 12 will rise until the original pressure equilibrium level 38 is reached, as indicated in FIG. 8. At this point, continuous administration automatically resumes. Thus after hospital personnnel injects necessary medicament into the chamber and properly dilutes it, the personal presence of hospital personnel is no longer required. The time and cost savings provided by the use of the burette chamber of this invention in an IV administration set are therefore substantial.

Although an illustrative embodiment of the invention has been shown and described, it is to be understood that various modifications and substitutions may be made by those skilled in the art without departing from the novel spirit and scope of the present invention.

What is claimed is:

1. A burette chamber adapted to administer intravenous solution to a patient and selectively permit, during the administration of intravenous solution, the injection of medicament, comprising, in combination: an airtight container having a secondary compartment for dispensing intravenous solution, a primary compartment for automatically providing intravenous solution to the secondary compartment in response to the amount of fluid in said secondary compartment and a wall member separating said compartments; a first inlet connected to said container and communicating with said primary compartment; means for coupling said first inlet to a primary solution container; an injection site connected to said airtight container and communicating with the interior thereof for the injection of medicament into said airtight container; said wall member defining an opening for communication between said primary compartment and said secondary compartment; a tube connected to said inlet and extending downwardly therefrom to the lower portion of said primary compartment to permit the intravenous solution to be displaced up into the tube towards the primary solution container as medicament is injected through said injection site into the airtight container; and a drip chamber connected to said airtight container and forming an outlet therewith.

2. A burette chamber as described in claim 1, wherein said injection site communicates with said secondary compartment.

3. A burette chamber as described in claim 1, wherein said container has molded volume indicia thereon.

4. A burette chamber as described in claim 1, wherein the primary and secondary compartments have different light-transmissive surfaces.

5. An administration set for administering an intravenous solution to a patient, said set including an airtight container comprising a primary compartment, a secondary compartment, and a wall member separating said compartments; a first inlet connected to said container and communicating with said primary compartment; a tube connected to said first inlet and extending downwardly therefrom to the lower portion of said primary compartment; an injection site connected to said container and communicating with the interior of said secondary compartment for permitting the injection of medicament therein; said wall member defining an opening for communication between said primary compartment and said secondary compartment to permit the intravenous solution to flow from the primary compartment into the secondary compartment as the solution is being administered to a patient; and a drip chamber connected to said container and forming an outlet therewith.

6. A method of administering an intravenous solution to a patient using an administration set which includes a burette chamber, a first inlet connected to said chamber, an injection site connected to said chamber, a drip chamber connected to said burette chamber and forming an outlet therewith, the improvement comprising the steps of: connecting an outlet tube to a patient; connecting a primary solution container containing primary solution to said first inlet; filling a first portion of the burette chamber separated from a second portion of said burette chamber with primary solution; permitting the primary solution to flow into said second portion until pressure equilibrium is reached, permitting flow of the primary solution through the said outlet to the patient; injecting medicament into the injection site to mix with the primary solution in said second portion; maintaining pressure equilibrium by reducing the level of the primary solution in the first portion with the primary solution being displaced up into said tube into said primary solution container; and permitting the flow of medicament and the primary solution mixture from said outlet to the patient.

7. A method of administration as described in claim 6, including the step of automatically continuing the administration of the primary solution to the patient as the primary solution level rises in the primary compartment and spills over into the secondary compartment, after the medicament in the secondary compartment is administered to the patient.

* * * * *